United States Patent
Frühauf et al.

(10) Patent No.: US 9,126,041 B2
(45) Date of Patent: *Sep. 8, 2015

(54) REDUCTION OF TRANSIENT SOUNDS IN HEARING IMPLANTS

(71) Applicant: MED-EL Elektromedizinische Geraete GmbH, Innsbruck (AT)

(72) Inventors: Florian Frühauf, Rinn (AT); Ernst Aschbacher, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/488,409

(22) Filed: Sep. 17, 2014

(65) Prior Publication Data
US 2015/0005845 A1 Jan. 1, 2015

Related U.S. Application Data

(63) Continuation of application No. 13/975,487, filed on Aug. 26, 2013, now Pat. No. 8,929,994.

(60) Provisional application No. 61/693,356, filed on Aug. 27, 2012.

(51) Int. Cl.
*A61N 1/00* (2006.01)
*A61N 1/36* (2006.01)

(52) U.S. Cl.
CPC ........ *A61N 1/36032* (2013.01); *H04R 2225/67* (2013.01); *H04R 2430/03* (2013.01)

(58) Field of Classification Search
CPC . A61N 1/36032; A61B 5/0484; A61B 5/0482
See application file for complete search history.

(56) References Cited

U.S. PATENT DOCUMENTS 6,348,070 B1 2/2002 Teissl .................. 623/11.11
6,594,525 B1 7/2003 Zierhofer .................. 607/57

(Continued)

FOREIGN PATENT DOCUMENTS

EP 1371263 12/2010 ............ H04R 25/00
WO WO 99/53615 10/1999 ............ H03H 21/00

OTHER PUBLICATIONS

U.S. Patent and Trademark Office, Officer Shane Thomas, International Search Report and Written Opinion, PCT/US13/56559, date of mailing Nov. 13, 2013, 11 pages.

(Continued)

*Primary Examiner* — Robert N Wieland
(74) *Attorney, Agent, or Firm* — Sunstein Kann Murphy & Timbers LLP

(57) ABSTRACT

A method is described for generating electrode stimulation signals for electrode contacts in a cochlear implant electrode array. An input audio signal is processed to generate band pass channel signals that each represent an associated band of audio frequencies. A channel envelope is extracted from each channel signal. The input audio signal and the channel envelopes are processed to produce transient reduced envelopes based on: i. determining for each channel envelope a normalized channel-specific transient indicator characterizing transient noise present in the channel signal, ii. determining a combined transient indicator as a function of the channel-specific transient indicators, and iii. applying a channel-specific gain to the channel envelopes as a function of the combined transient indicator to produce the transient reduced envelopes. The transient reduced envelopes are then used to generate electrode stimulation signals to the electrode contacts.

20 Claims, 8 Drawing Sheets

(56) References Cited

U.S. PATENT DOCUMENTS

| | | | |
|---|---|---|---|
| 7,353,169 B1 | 4/2008 | Goodwin et al. | 704/224 |
| 7,435,228 B2 | 10/2008 | Martin | 600/559 |
| 7,725,315 B2 | 5/2010 | Hetherington et al. | 704/233 |
| 7,869,994 B2 | 1/2011 | Nongpiur et al. | 704/226 |
| 7,953,490 B1 | 5/2011 | Fridman | 607/57 |
| 8,065,016 B2 | 11/2011 | Paolini et al. | 607/57 |
| 2005/0187592 A1 | 8/2005 | Seligman et al. | 607/57 |
| 2005/0209657 A1 | 9/2005 | Chung et al. | 607/57 |
| 2007/0239227 A1 | 10/2007 | Fridman | 607/57 |
| 2009/0154746 A1* | 6/2009 | Fischer | 381/317 |
| 2010/0191309 A1 | 7/2010 | Schleich | 607/57 |
| 2011/0004274 A1 | 1/2011 | Schleich et al. | 607/57 |
| 2012/0209351 A1 | 8/2012 | Meister et al. | 607/57 |

OTHER PUBLICATIONS

Hochmair, et al., "MED-EL Cochlear Implants: State of the Art and a Glimpse into the Future", *Trends in Amplification*, vol. 10, No. 4, Dec. 2006, pp. 201-219, 19 pages.

Hernandez, et al., "An Assessment of Everyday Noises and Their Annoyance", *Hearing Review*, 2006, 13(7), 6 pages.

* cited by examiner

REDUCTION OF TRANSIENT SOUNDS IN HEARING IMPLANTS

This application is a continuation of co-pending U.S. patent application Ser. No. 13/975,487, filed Aug. 26, 2013, and issued as U.S. Pat. No. 8,929,994, which in turn claimed priority from U.S. Provisional Patent Application 61/693,356, filed Aug. 27, 2012, which is incorporated herein by reference.

FIELD OF THE INVENTION

The present invention relates to hearing implant systems such as cochlear implants, and specifically to the signal processing used therein.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrodes on its surface that provide selective stimulation of the cochlea 104.

In cochlear implants today, a relatively small number of electrodes are each associated with relatively broad frequency bands, with each electrode addressing a group of neurons through a stimulation pulse the charge of which is derived from the instantaneous amplitude of the envelope within that frequency band. In some coding strategies, stimulation pulses are applied at constant rate across all electrodes, whereas in other coding strategies, stimulation pulses are applied at an electrode-specific rate.

Various signal processing schemes can be implemented to produce the electrical stimulation signals. Signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, and compressed analog (CA) signal processing. For example, in the CIS approach, signal processing for the speech processor involves the following steps:
(1) splitting up of the audio frequency range into spectral bands by means of a filter bank,
(2) envelope detection of each filter output signal,
(3) instantaneous nonlinear compression of the envelope signal (map law).

According to the tonotopic organization of the cochlea, each stimulation electrode in the scala tympani is associated with a band pass filter of the external filter bank. For stimulation, symmetrical biphasic current pulses are applied. The amplitudes of the stimulation pulses are directly obtained from the compressed envelope signals. These signals are sampled sequentially, and the stimulation pulses are applied in a strictly non-overlapping sequence. Thus, as a typical CIS-feature, only one stimulation channel is active at one time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit. Each output of the CIS band pass filters can roughly be regarded as a sinusoid at the center frequency of the band pass filter which is modulated by the envelope signal. This is due to the quality factor ($Q \approx 3$) of the filters. In case of a voiced speech segment, this envelope is approximately periodic, and the repetition rate is equal to the pitch frequency.

In the existing CIS-strategy, only the envelope signals are used for further processing, i.e., they contain the entire stimulation information. For each channel, the envelope is represented as a sequence of biphasic pulses at a constant repetition rate. A characteristic feature of CIS is that this repetition rate (typically 1.5 kpps) is equal for all channels and there is no relation to the center frequencies of the individual channels. It is intended that the repetition rate is not a temporal cue for the patient, i.e., it should be sufficiently high, so that the patient does not perceive tones with a frequency equal to the repetition rate. The repetition rate is usually chosen at greater than twice the bandwidth of the envelope signals (Nyquist theorem).

Another cochlear implant stimulation strategy that transmits fine time structure information is the Fine Structure Processing (FSP) strategy by Med-El. Zero crossings of the band pass filtered time signals are tracked, and at each negative to positive zero crossing a Channel Specific Sampling Sequence (CSSS) is started. Typically CSSS sequences are only applied on the first one or two most apical channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference.

FIG. 2 shows major functional blocks in the signal processing arrangement typical of existing cochlear implant (CI) systems wherein band pass signals containing stimulation timing and amplitude information are assigned to stimulation electrodes. Preprocessor Filter Bank 201 pre-processes an initial acoustic audio signal, e.g., automatic gain control, noise reduction, etc. Each band pass filter in the Preprocessor Filter Bank 201 is associated with a specific band of audio frequencies so that the acoustic audio signal is filtered into some N band pass signals, $B_1$ to $B_N$ where each signal corresponds to the band of frequencies for one of the band pass filters.

The band pass signals $B_1$ to $B_N$ are input to a Stimulation Pulse Generator 202 which extracts signal specific stimulation information—e.g., envelope information, phase information, timing of requested stimulation events, etc.—into a set of N stimulation event signals $S_1$ to $S_N$, which represent electrode specific requested stimulation events. For example, channel specific sampling sequences (CSSS) may be used as described in U.S. Pat. No. 6,594,525, which is incorporated herein by reference.

Pulse Mapping Module 203 applies a non-linear mapping function (typically logarithmic) to the amplitude of the each band-pass envelope. This mapping function typically is adapted to the needs of the individual CI user during fitting of the implant in order to achieve natural loudness growth. This may be in the specific form of functions that are applied to each requested stimulation event signal $S_1$ to $S_N$ that reflect patient-specific perceptual characteristics to produce a set of electrode stimulation signals $A_1$ to $A_M$ that provide an optimal electric representation of the acoustic signal.

The Pulse Mapping Module 203 controls loudness mapping functions. The amplitudes of the electrical pulses are derived from the envelopes of the assigned band pass filter outputs. A logarithmic function with a form-factor C typically may be applied to stimulation event signals $S_1$ to $S_N$ as a loudness mapping function, which generally is identical across all the band pass analysis channels. In different systems, different specific loudness mapping functions other than a logarithmic function may be used, though still just one identical function is applied to all channels to produce the electrode stimulation signals $A_1$ to $A_M$ outputs from the Pulse Mapping Module 203.

Patient specific stimulation is achieved by individual amplitude mapping and pulse shape definition in Pulse Shaper 204 which develops the set of electrode stimulation signals $A_1$ to $A_M$ into a set of output electrode pulses $E_1$ to $E_M$ to the electrodes in the implanted electrode array which stimulate the adjacent nerve tissue.

Background noise weakens the speech intelligibility of hearing aid and cochlear implant users. According to Hernandez et al., *An Assessment Of Everyday Noises And Their Annoyance*, Hearing Review, 2006, 13(7), 16-20 (incorporated herein by reference), 33% of sensate background noise is formed by transient sounds such as computer key strokes, slamming doors, dish clattering, etc., all of which are unpleasant and reduce listening comfort (See also, German Patent DE 102005043314). The transient noise reduction algorithms in existing hearing aids such as the AntiShock from Unitron Connect and the SoundSmoothing from Siemens have been found to yield an improvement in the listening experience. See DiGiovanni et al., *Effects of Transient-Noise Reduction Algorithms on Speech Intelligibility and Ratings of Hearing Aid Users*, American Journal of Audiology, first published on Sep. 22, 2011 as doi:10.1044/1059-0889(2011/10-0007), incorporated herein by reference. Transient noise reduction is also sought in other applications. For example, sound quality for car passengers may be improved by reducing the transient road noise created when tires strike an obstruction. See U.S. Pat. No. 7,725,315, incorporated herein by reference. Likewise, in high-end audio equipment that renders audio data, the potential to modify transient features like drumsticks hitting a drum is desired to meet different individual preferences in music listening. See U.S. Pat. No. 7,353,169, incorporated herein by reference.

In existing cochlear implants, the incorporation of a dual front-end automatic gain control (AGC) improves performance when intense transients occur. See, e.g., Stöbich et al., *Influence of Automatic Gain Control Parameter Settings on Speech Understanding of Cochlear Implant Users Employing the Continuous Interleaved Sampling Strategy*, Ear & Hearing, 1999, 20, 104-116, incorporated herein by reference. However the period of the AGC gain is too long to start a reduction at the onset of the transients and the amount of reduction is not sufficient.

Transient signals are characterized by a fast and steep rising envelope of the sound signal. Thus during the occurrence of a transient, the envelope has much higher values for a short time interval. In German Patent DE 102005043314, the steepness and/or the amplitude of the envelope of the sound signal are considered. If one or both of these values exceed certain thresholds, the sound signal is attenuated.

In European Patent EP 1371263 (incorporated herein by reference), the sound signal is transformed into K sub-signals in the frequency domain. Then, for each sub-signal, two or three sub-indices are calculated which are used to classify the present sound signal into the categories "stationary noise", "quasi stationary noise", "desired speech and music" and "transient noise". These sub-indices refer to intensity changes during a given time interval, the modulation frequency, and the duration of very similar intensities of the signal, respectively. According to the classified category, a gain function is calculated, that is used to suppress transient sounds or to enhance the SNR in case of the classified categories "stationary noise" or "quasi stationary noise".

In WO 99/53615 (incorporated herein by reference), a transient detector divides the input signal into at least two frequency bands. In each of these bands, the derivative and/or the amplitude of the envelope are compared to at least one threshold function to indicate a transient in the respective band. If a transient is detected in at least one band, the coefficients of an adaptive filter are changed in such a way that the transients in the input signal are reduced by filtering the delayed input signal with this determined adaptive filter. After the detector no longer detects a transient, the filter coefficients return to the values before the transient has appeared.

In U.S. Pat. No. 7,353,169, the spectral flux is used to determine frequency-specific indicators of transient features in high end audio equipment. According to these indicators, a modification of the corresponding transient features is applied to improve the impression of music. The user can decide on the amount, the frequency ranges, and the kind of modification (suppression or enhancement) he prefers.

U.S. Pat. No. 7,725,315 (incorporated herein by reference), describes using models of transient road noise based on a code book or a neural network to attenuate transient sounds.

U.S. Pat. No. 7,869,994 (incorporated herein by reference) describes an attenuation of certain wavelet coefficients based on a threshold to suppress transient sounds.

A possibility to reduce transient features in a cochlear implant system is to use hearing aid algorithms as proposed in U.S. 2005/0209657 (incorporated herein by reference).

In Stöbich 1999, a dual front-end AGC is proposed to reduce transient features.

SUMMARY OF THE INVENTION

Embodiments of the present invention are directed to methods, systems and software code for generating electrode stimulation signals for electrode contacts in a cochlear implant electrode array. An input audio signal is processed to generate band pass channel signals that each represent an associated band of audio frequencies. A channel envelope is extracted from each channel signal. The input audio signal and the channel envelopes are processed to produce transient reduced envelopes based on: i. determining for each channel envelope a normalized channel-specific transient indicator characterizing transient noise present in the channel signal, ii. determining a combined transient indicator as a function of the channel-specific transient indicators, and iii. applying a channel-specific gain to the channel envelopes as a function of the combined transient indicator to produce the transient reduced envelopes. The transient reduced envelopes are then used to generate electrode stimulation signals to the electrode contacts.

The channel-specific transient indicator may be based on a proportion of power of the channel envelope to power of the input audio signal and/or high-pass filtering the channel envelope. The combined transient indicator may be based on a combined product of the channel-specific transient indicators and/or a dependent function of the channel signals, which may reflect a limited frequency sub-range of the channel signals.

The channel-specific gains may be based on a single common gain function, a filter applied to the channel envelopes, and/or may reflect a signal-dependent suppression duration. A stationary noise reduction process may be applied to the channel envelopes before producing the transient reduced envelopes.

DETAILED DESCRIPTION OF SPECIFIC EMBODIMENTS

Embodiments of the present invention are directed to reduction of unpleasant transient sounds to improve the hearing comfort of cochlea implant users and enhance speech intelligibility in environments with significant transient background noise such as a cafeteria. Simulation results show that speech perception in quiet background conditions is unaffected.

Figure 1:
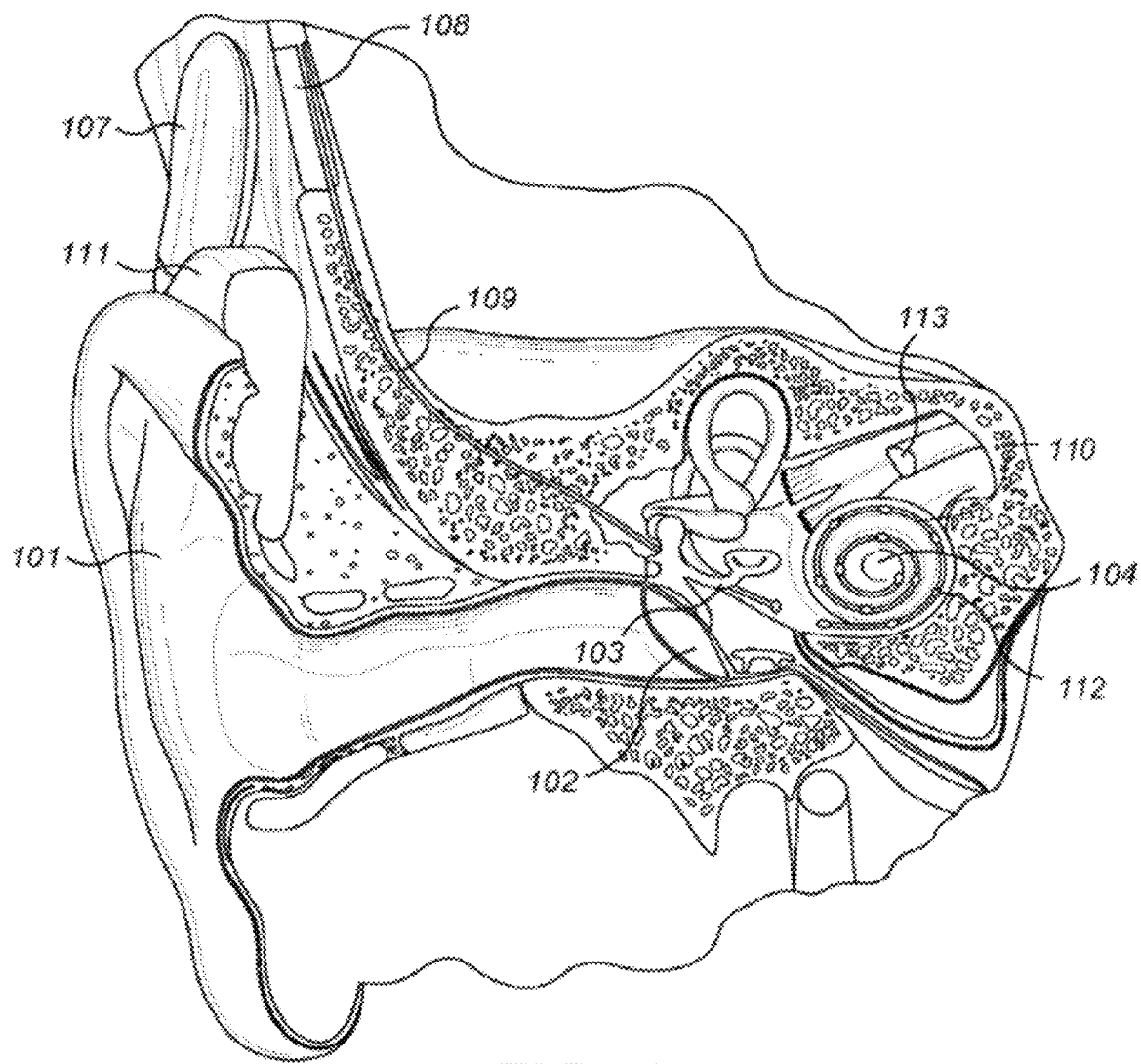
FIG. 1 shows the anatomy of a typical human ear and components in a cochlear implant system.
Figure 2:
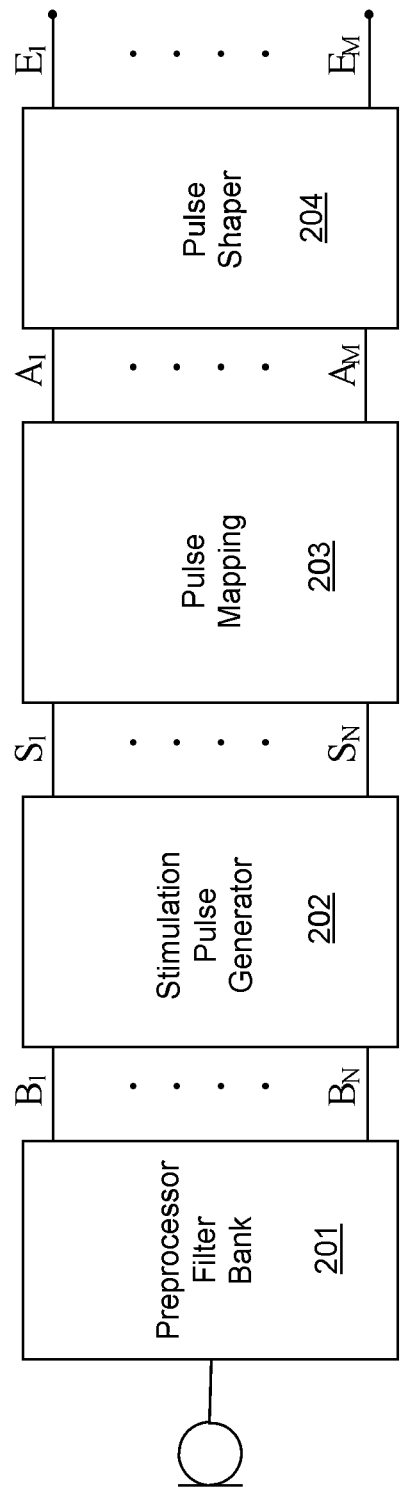
FIG. 2 shows major signal processing blocks of a typical cochlear implant system.
Figure 3:
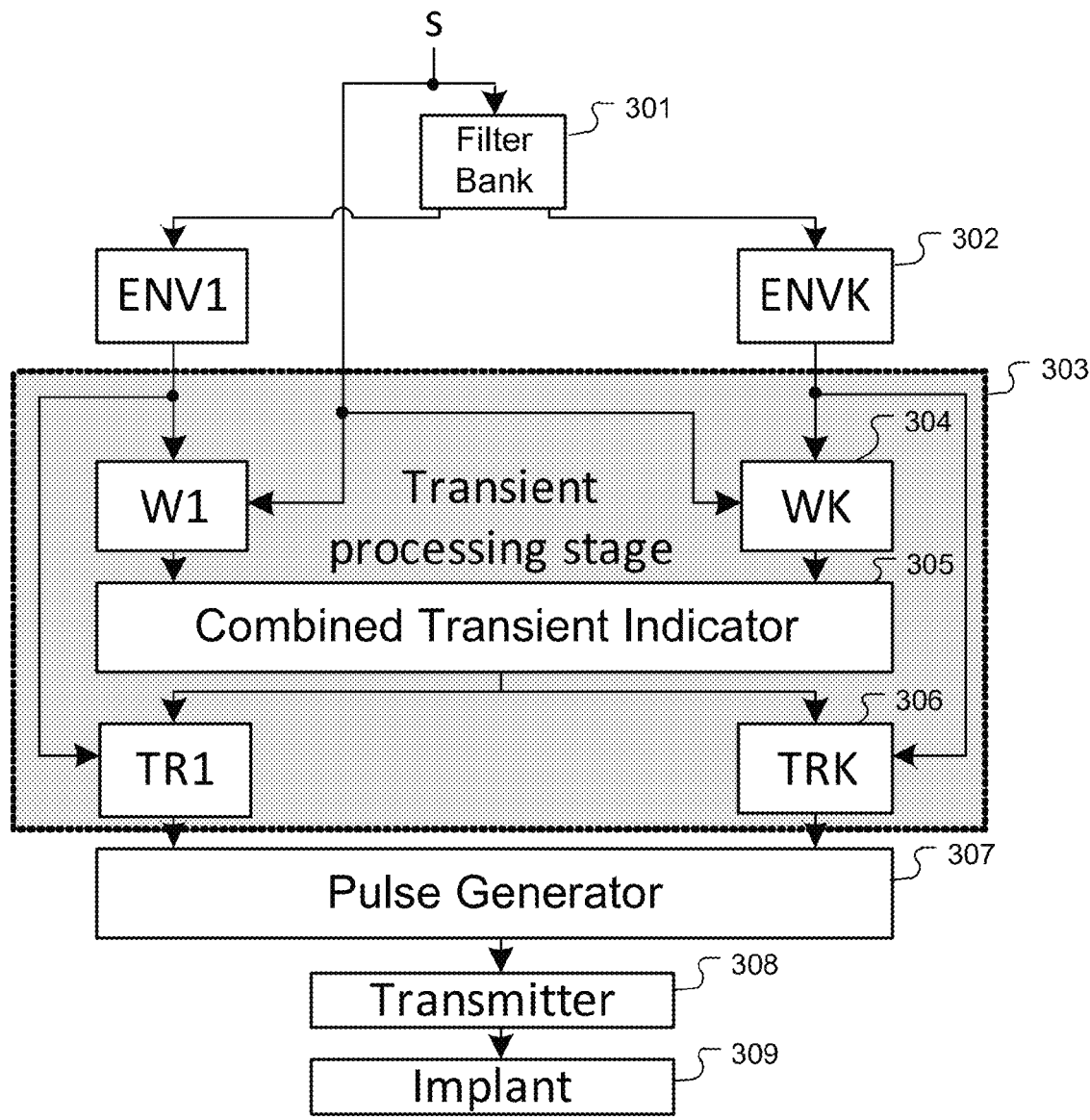
FIG. 3 shows various functional blocks in a signal processing arrangement according to an embodiment of the present invention.

FIG. 3 shows one specific embodiment for signal-processing in a cochlear implant using a transient processing stage. A digitized input audio signal s is processed by a filter bank 301 to generate K band pass channel signals that each represent an associated band of audio frequencies. Instead of a time-domain filter bank 301 another possibility to get a frequency domain sub-band splitting of the input audio signal s can be used, e.g., a FFT. Envelope modules 302 extract a channel envelope ENV1 to ENVK from each band pass channel signal. Transient reduction module 303 processes the input audio signal s and the channel envelopes ENV1 to ENVK as will be discussed in detail below to produce K transient reduced envelopes. Pulse generator 307 uses the transient reduced envelopes to generate electrode stimulation signals that the transmitter 308 provides to the electrode contacts in the implant 309.

Figure 4:
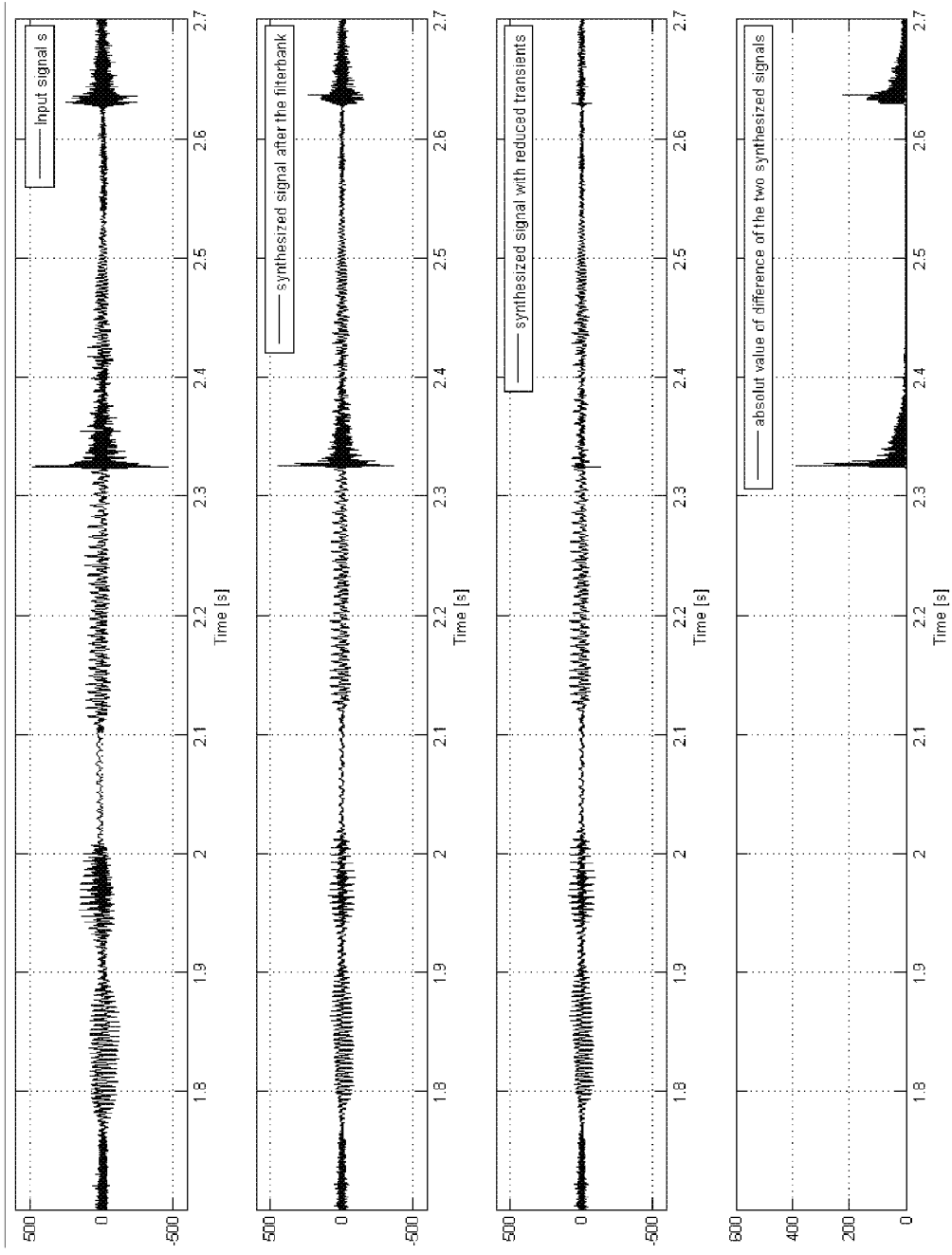
FIG. 4 is a graph showing an example of a speech input signal with two noise transients.

FIG. 4 is a graph showing an example of a speech input signal with two noise transients. The top plot shows an input speech signal with two noise transients resulting from clattering which are located in the time intervals [2.32, 2.37] and [2.63, 2.68] seconds. The second plot shows the synthesized signal after passing the filter bank 301, and the third plot shows the resulting synthesized transient reduced envelope output signal from the transient reduction module 303. The bottom plot shows the difference between these two synthesized signals showing that the speech parts of the signals are not affected by the transient reduction module 303, only the two noise transients are reduced.

Figure 5:
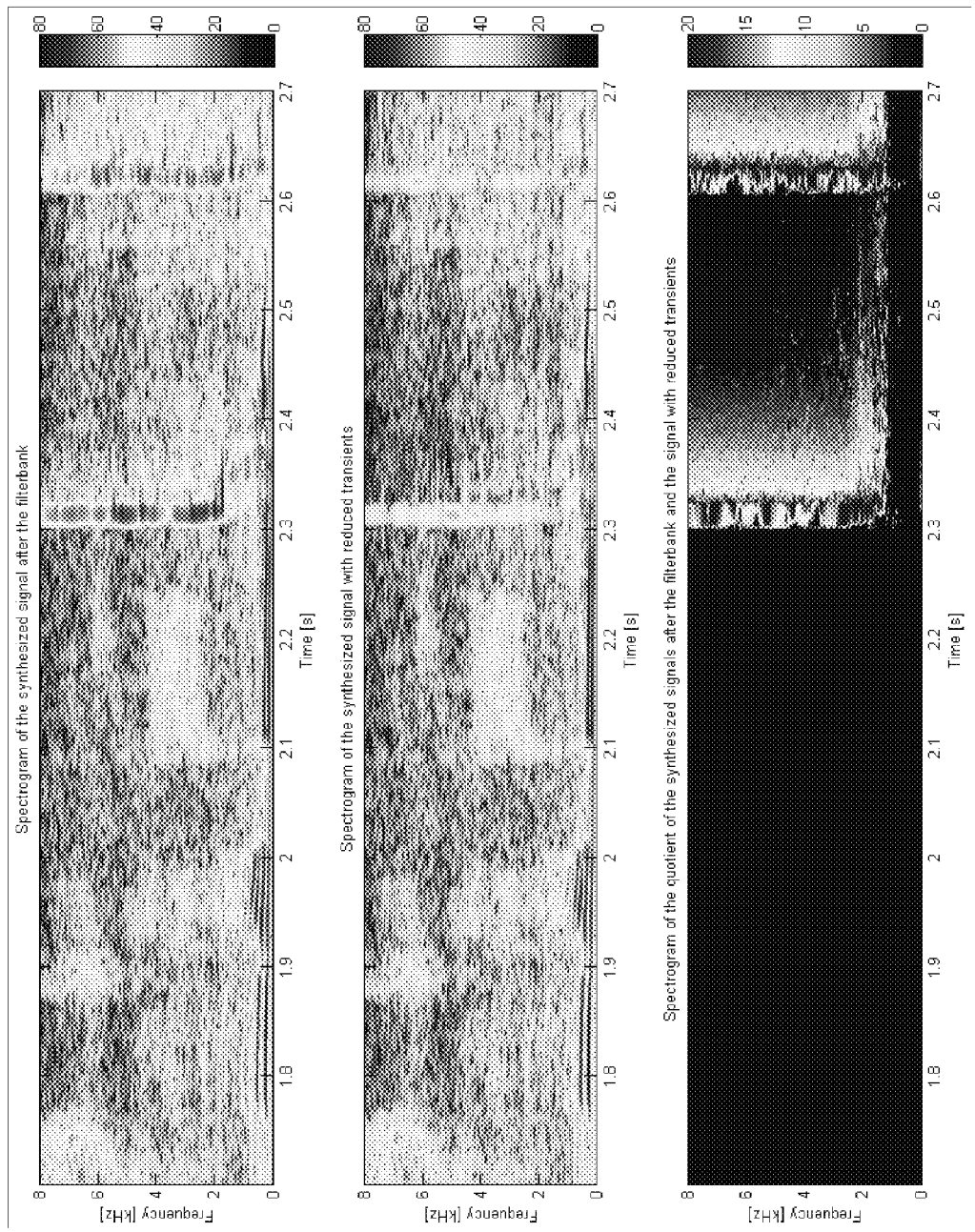
FIG. 5 shows the effects of transient reduction in the frequency domain.

FIG. 5 demonstrates the effect of the transient reduction in the frequency domain. The top image shows the spectrogram of the synthesized signal after the filter bank 301, which is presented in the second plot of FIG. 4, where it is clear that the main energy of the noise transients is located in the high frequency regions. The second image in FIG. 5 shows the spectrogram of the synthesized transient reduced envelope output signal from the transient reduction module 303, and the bottom image shows the spectrogram of the quotient of these two synthesized signals in which it is clear that the speech features are preserved while the high frequency elements of the noise transients are reduced.

Considering the transient reduction module 303 in greater detail, normalized indicator modules 304 receive the input audio signals s and the corresponding k-th channel envelope to produce normalized channel-specific transient indicators characterizing transient noise present in the channel signal. These can be determined as:

$$v_k = a_k \cdot \left(\frac{envelope_k}{z}\right)^2$$

where $a_k$ is a non-negative channel-specific parameter which controls the size of $v_k$ depending, for instance, on the settings of the filter bank 301. The signal z results from low-pass filtering and rectifying the signal s, i.e., $z = LP(|s|)$. The normalization of the envelope with the signal z is necessary because then $v_k$ describes the proportion of the power of a transient signal in the k-th channel envelope related to the power of the whole signal. Moreover, the normalization ensures that the reduction of the noise transient is independent of the loudness of the audio input signal s.

Figure 6:
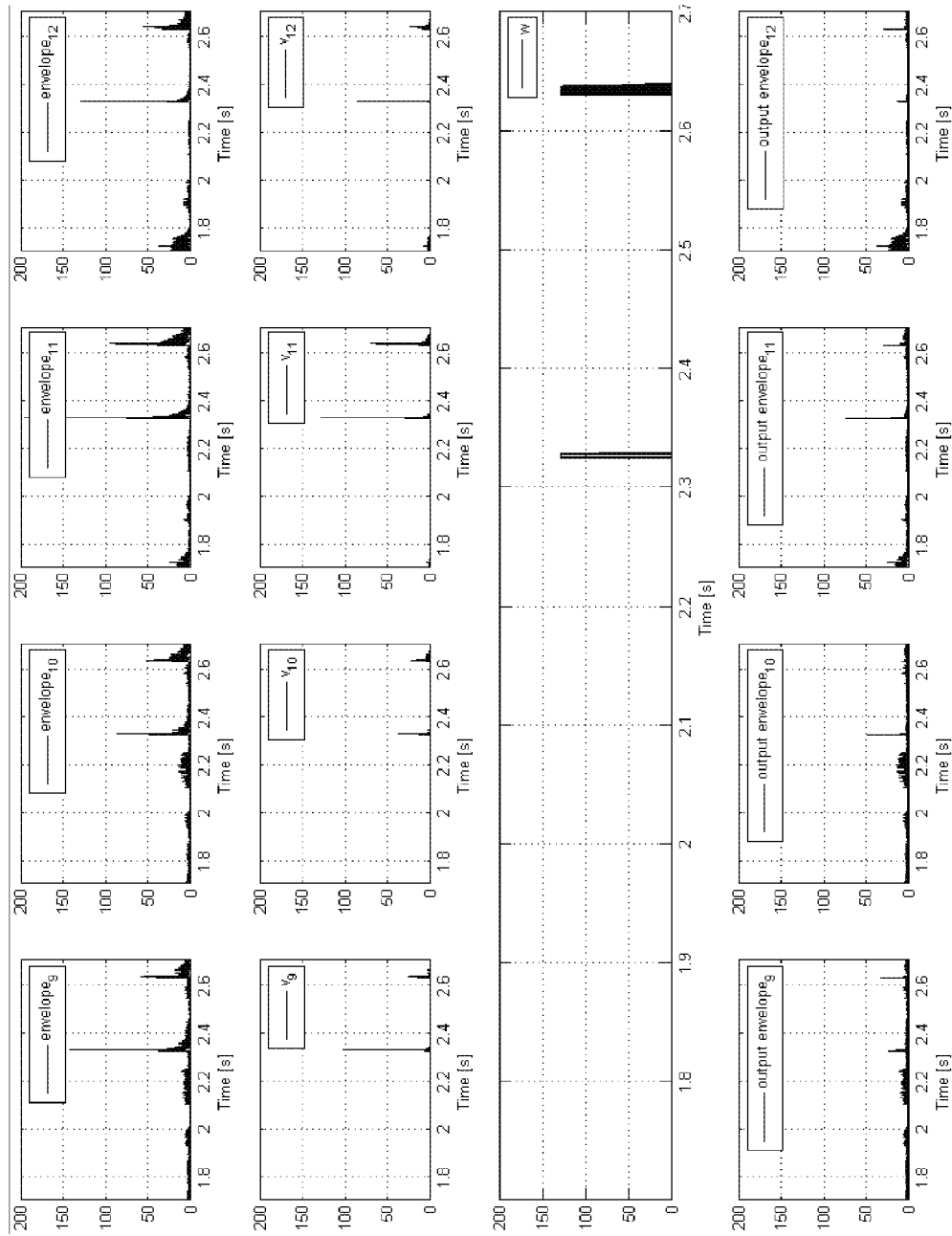
FIG. 6 shows examples of channel envelope signals in transient processing according to embodiments of the present invention.

The top row of FIG. 6 shows the input envelopes of channels 9 to 12 resulting from the audio input signal s that is plotted in the top of FIG. 4. The boundary frequencies of these channels are 2294, 3201, 4445, 6153 and 8500 Hz. The second row in FIG. 6 presents the corresponding channel-specific transient indicators $v_9$ to $v_{12}$. Only the locations of the noise transients $v_k$ all have large values. Instead of using the envelope value to determine the channel-specific transient indicators $v_1, \ldots, v_K$, a specific embodiment could use a high-pass filtered envelope, for example, the first derivative of the envelope. In addition or alternatively, the information of both features can be used to determine the channel specific indicators $v_1, \ldots, v_K$, that is, a combination of the value and the high-pass filtered value of the envelope.

Combined transient indicator module 305 receives as inputs the channel-specific transient indicators $v_1, \ldots, v_K$ and develops an output signal combined transient indicator w. Noise transient signals (e.g., from dish clattering or rustling paper) typically have high envelopes in all signal channels higher than approximately 1 kHz. Thus, the channel-specific transient indicators $v_k$ of these channels also have high values. This is not the case for consonants and plosives such as "s", "sch", "t", "tz" where only some of the channel-specific indicators have high values. Given a set of channels: M={j: the lower boundary frequency of channel j is greater than 1 kHz}, then a high value of the signal $$w = \prod_{j \in M} v_j$$

relates to the presence of a noise transient signal, whereas the combined transient indicator w has relatively low values in the cases of consonants, plosives and fricatives. The third plot in FIG. 6 shows the indicator $$w = \prod_{j=9}^{12} v_j,$$

which is greater than 0 at the positions of the onset of the noise transient.

Instead of the multiplication $$w = \prod_{j \in M} v_j,$$

an embodiment could use any function $f(v_1, \ldots, v_K)$ with the following properties:
  Only the selected set of channels M={j: channel j is located within a certain frequency range} influence the result.
  If one of the channel-specific transient indicators $v_k$, k∈M has low values, then $f$ is small, too.
  If all the channel-specific transient indicators $v_k$, k∈M have high values, then $f$ is high.
  If all the channel-specific transient indicators $v_k$, k∈M/{j} have constant values greater than zero, then $f$ is a monotone increasing function of $v_1$.
The selected set of channels M can differ between the output channels. This means for example, distinguishing between transients in the low, middle and high frequency channels to reduce the corresponding low, middle and high transient features. Then the combined transient indicator module 305 has multiple combined transient indicator outputs $w_k$.

Channel-specific gain module 306 receives the combined transient indicator w and the corresponding envelope of the k-th channel to produce transient reduced envelope signals. Channel specific gain are determined and applied to the channel envelopes to suppress noise transients. Depending on the combined transient indicator w, an actual gain value is determined: g=max(1−σ·w,l), where 0<l≤1 is the lower bound of the suppression factor g and σ is a channel-specific positive constant parameter which determines the amount of the suppression in the channel. Next, the gain function h is calculated. This function should immediately reduce the noise transients when they occur, but the gain function h also should increase with an exponential decay (fast attack, slow release). This leads to the following approach:

$h[n]=(1-b_r)\cdot h[n-1]+b_r\cdot g[n]$, if $h[n-1]<g[n]$ (release)

$h[n]=b_a\cdot h[n-1]+(1-b_a)\cdot g[n]$, if $h[n-1]\geq g[n]$ (attack)

with $0\leq b_a, b_r \ll 1$. Note that a time-index n is included since a feedback loop exists. A small value of $b_a$ results in a fast decay of h[n]. Thus, the reduction of the transient signal starts immediately. If h[n−1]<g[n], then the suppression factor h increases slowly as determined by the release-time constant $b_r$. The transient reduced output envelopes are then generated by multiplying h by the input envelope signals. The bottom row of FIG. 6 shows the resulting transient-reduced envelopes.

Instead of the calculation of one gain function h, coefficients of a linear FIR filter or a nonlinear filter can be calculated that are applied to the envelope signal. The method for the calculation of the gain can be modified in such a way that the duration of the suppression is signal dependent, e.g., replacing the parameter $b_r$ by a function of $b_r(w, v_1, \ldots, v_K)$. The attack time then depends on the constant parameter $b_a$. This could be changed by modifying the calculation of the gain function or by a signal dependent parameter $b_a$. The application of the gain to the envelope can be different from a simple multiplication, for example a FIR filter or an N-of-M type cochlear implant coding strategy can be controlled by the combined transient indicator w.

Figure 7:
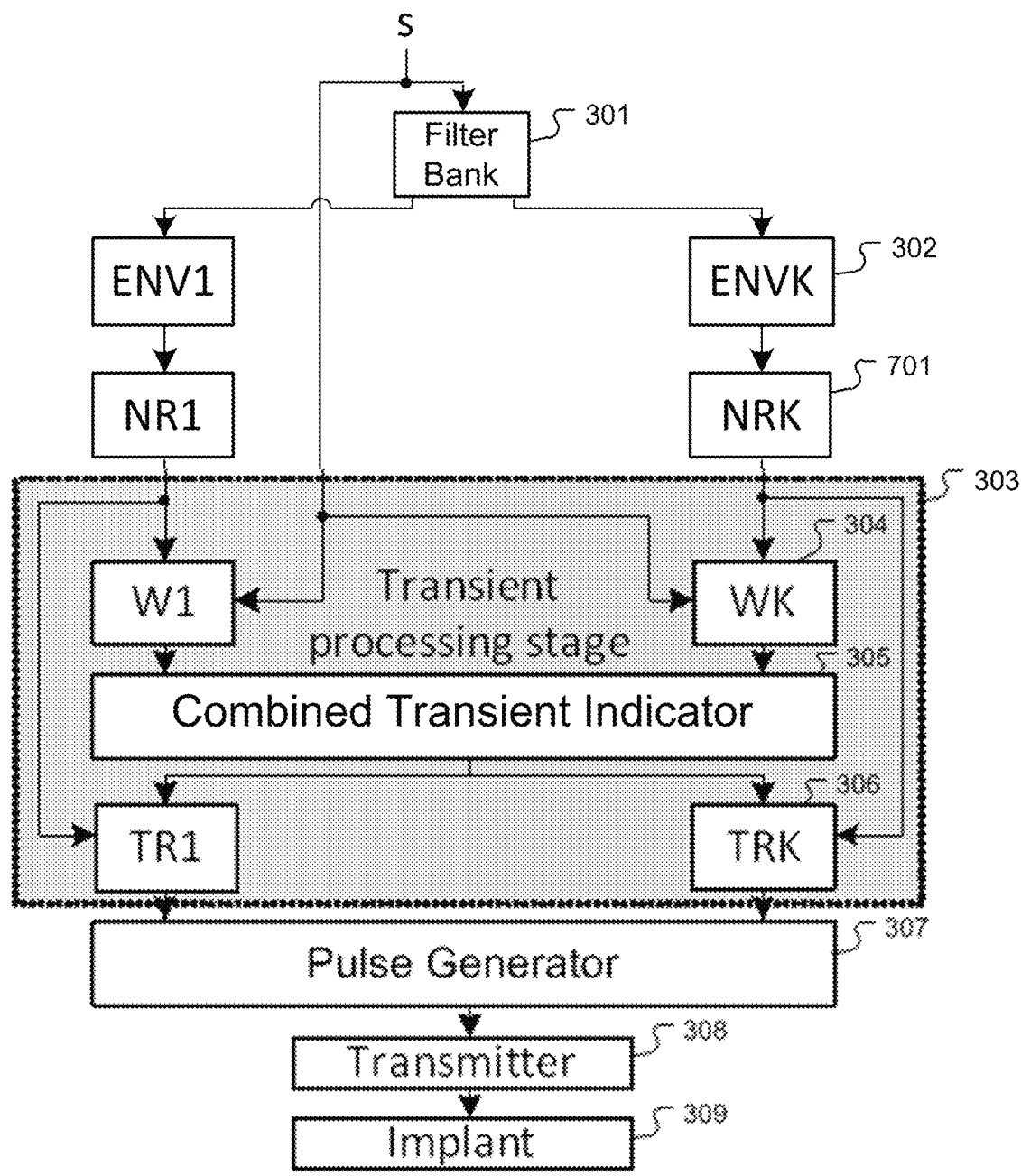
FIG. 7 shows various functional blocks in a signal processing arrangement according to an embodiment including stationary noise reduction.

FIG. 7 shows a noise reduction arrangement which includes a stationary noise reduction module 701 in front of the transient reduction module 303. The signals from the stationary noise reduction module 701 influence the determination of the combined transient indicator w. So if, for example, a voice activity detector indicates the presence of speech, then it is assumed that a speech feature is present in that channel and this is not reduced by the transient reduction.

The foregoing transient noise reduction techniques are different from the other earlier arrangements discussed in the Background section above. In DE 102005043314, the reduction of transients is done in the time domain without considering frequency specific features; i.e., the processing is done without splitting the signal into frequency parts. Furthermore, a threshold is used to determine if the signal has a transient feature, which is not the case in the above described method.

In EP 1371263 a classification is performed into the categories "stationary noise", "quasi stationary noise", "desired speech and music" and "transient noise". And furthermore, the sub-indices to classify the signals are different what is described above.

WO 99/53615 uses a threshold to indicate a transient signal. And only a single gain is applied to the input signal s, whereas the embodiments discussed above apply the channel-specific gains on each of the channel envelopes.

In U.S. Pat. No. 7,353,169 the spectral flux constitutes a norm over the frequencies at each time of the first derivate in time. These norms differ from what is described above that uses multiplication over the frequencies, which is not a norm.

U.S. Pat. No. 7,725,315 uses special features of transient noise in a car to detect transients via a codebook or a neural network. U.S. Pat. No. 7,869,994 uses a wavelet transformation. These are completely different compared from the transient reduction described above. In US 2005/0209657 no algorithm is proposed to reduce noise transient signals, and the only discussion is of using in cochlear implants the algorithms employed by hearing aids.

Figure 8:
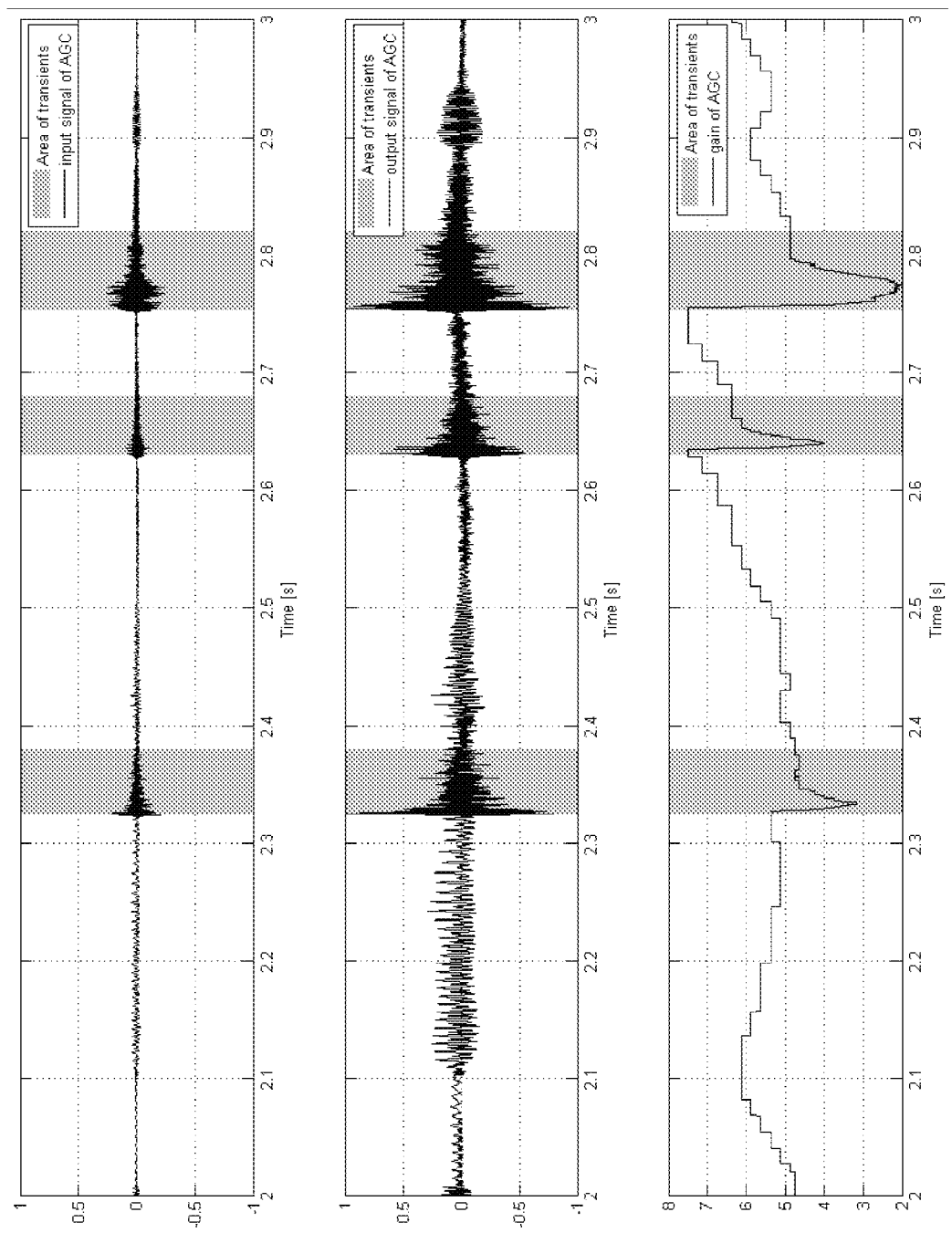
FIG. 8 shows application of dual front-end AGC to an audio signal.

Stöbich 1999 proposed using a dual front-end AGC to reduce transient features. FIG. 8 shows the result of the dual front-end AGC. The top plot shows the input signal which is a mixed audio signal of speech with three instances of a dish clattering (shaded grey). In the middle and bottom plots the output signal and the corresponding gain of the AGC respectively are shown. It can be seen that the gain is reduced when a noise transient occurs, but the onset is missed and the amount of the reduction is not sufficiently high compared to the suppression results in the example in FIG. 5.

The prior art does not describe normalization with the low-pass filtered signal z, and most of the other approaches use a threshold to decide if a noise transient is contained in the audio input signal. And the embodiments of the present invention described above refrain completely from using any kind of threshold.

In certain cases, an embodiment may erroneously detect consonants as noise transients, undesirably damping such consonants and impairing their perception. Simulation results yielded a maximum false detection rate below 5 percent if a stationary noise reduction algorithm is added into the signal processing in front of the transient reduction module. For bilaterally implanted users, the interaural level differences can be changed in certain cases, degrading the localization of transient sounds Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A computer program product implemented in a non-transitory, tangible computer readable storage medium for generating electrode stimulation signals for electrode contacts in a cochlear implant electrode array, the product comprising:
   program code for processing an input audio signal to generate a plurality of band pass channel signals each representing an associated band of audio frequencies;
   program code for extracting a channel envelope from each channel signal;
   program code for processing the input audio signal and the channel envelopes to produce transient reduced envelopes based on:
      i. determining for each channel envelope a normalized channel-specific transient indicator characterizing transient noise present in the channel signal,
      ii. determining a combined transient indicator as a function of the channel-specific transient indicators, and
      iii. applying a channel-specific gain to the channel envelopes as a function of the combined transient indicator to produce the transient reduced envelopes; and
   program code for using the transient reduced envelopes to generate electrode stimulation signals to the electrode contacts.

2. A product according to claim 1, wherein the channel-specific transient indicator is based on a proportion of power of the channel envelope to power of the input audio signal.

3. A product according to claim 1, wherein the channel-specific transient indicator is based on high-pass filtering the channel envelope.

4. A product according to claim 1, wherein the combined transient indicator is based on a combined product of the channel-specific transient indicators.

5. A product according to claim 1, wherein the combined transient indicator is based on a dependent function of the channel signals.

6. A product according to claim 5, wherein the function reflects a limited frequency sub-range of the channel signals.

7. A product according to claim 1, wherein the channel-specific gains are based on a single common gain function.

8. A product according to claim 1, wherein the channel-specific gains are based on a filter applied to the channel envelopes.

9. A product according to claim 1, wherein the channel specific gains reflect a signal-dependent suppression duration.

10. A product according to claim 1, further comprising:
program code for applying a stationary noise reduction process to the channel envelopes before producing the transient reduced envelopes.

11. A signal processing arrangement for generating electrode stimulation signals for electrode contacts in a cochlear implant electrode array, the arrangement comprising:
a filter bank pre-processor configured to process an input audio signal to generate a plurality of band pass channel signals each representing an associated band of audio frequencies;
a channel envelope module configured to extract a channel envelope from each channel signal;
a transient reduction module configured to process the input audio signal and the channel envelopes to produce transient reduced envelopes based on:
  i. determining for each channel envelope a normalized channel-specific transient indicator characterizing transient noise present in the channel signal,
  ii. determining a combined transient indicator as a function of the channel-specific transient indicators, and
  iii. applying a channel-specific gain to the channel envelopes as a function of the combined transient indicator to produce the transient reduced envelopes; and
a stimulation signal generator configured to use the transient reduced envelopes to generate electrode stimulation signals to the electrode contacts.

12. An arrangement according to claim 11, wherein the transient reduction module determines the channel-specific transient indicators based on a proportion of power of the channel envelope to power of the input audio signal.

13. An arrangement according to claim 11, wherein the transient reduction module determines the channel-specific transient indicator based on high-pass filtering the channel envelope.

14. An arrangement according to claim 11, wherein the transient reduction module determines the combined transient indicator based on a combined product of the channel-specific transient indicators.

15. An arrangement according to claim 11, wherein the transient reduction module determines the combined transient indicator based on a dependent function of the channel signals.

16. An arrangement according to claim 15, wherein the function reflects a limited frequency sub-range of the channel signals.

17. An arrangement according to claim 11, wherein the transient reduction module bases the channel-specific gains on a single common gain function.

18. An arrangement according to claim 11, wherein the transient reduction module bases the channel-specific gains on a filter applied to the channel envelopes.

19. An arrangement according to claim 11, wherein the transient reduction module applies channel specific gains that reflect a signal-dependent suppression duration.

20. An arrangement according to claim 11, further comprising:
a stationary noise reduction module before the transient noise reduction module configured to apply a stationary noise reduction process to the channel envelopes.

* * * * *